United States Patent
Isobe et al.

(12)

(10) Patent No.: US 8,273,906 B2
(45) Date of Patent: Sep. 25, 2012

(54) METHOD FOR PRODUCING GLYCOSIDE AGLYCONE

(75) Inventors: Yosuke Isobe, Tokyo (JP); Shuichi Kamo, Tokyo (JP); Toshiro Sato, Tokyo (JP); Hiroyuki Yoshida, Osaka (JP)

(73) Assignee: J-Oil Mills, Inc. (JP)

( * ) Notice: Subject to any disclaimer, the term of this patent is extended or adjusted under 35 U.S.C. 154(b) by 445 days.

(21) Appl. No.: 12/665,712

(22) PCT Filed: Jun. 13, 2008

(86) PCT No.: PCT/JP2008/001525
§ 371 (c)(1), (2), (4) Date: Dec. 19, 2009

(87) PCT Pub. No.: WO2008/155890
PCT Pub. Date: Dec. 24, 2008

(65) Prior Publication Data
US 2010/0191003 A1 Jul. 29, 2010

(30) Foreign Application Priority Data
Jun. 21, 2007 (JP) ................................. 2007-164018

(51) Int. Cl.
*C07D 309/32* (2006.01)
*C07D 311/30* (2006.01)
*C07C 35/34* (2006.01)
*C07C 49/377* (2006.01)

(52) U.S. Cl. ......... 549/403; 549/420; 552/262; 568/817

(58) Field of Classification Search .................. 549/403, 549/420; 552/262; 568/817
See application file for complete search history.

(56) References Cited

U.S. PATENT DOCUMENTS
4,684,740 A 8/1987 Higuchi et al.

FOREIGN PATENT DOCUMENTS

| | | |
|---|---|---|
| CN | 1359903 | 7/2002 |
| EP | 1582512 | 10/2005 |
| JP | 61-218590 | 9/1986 |
| JP | 3-120209 | 5/1991 |
| JP | 4-283518 | 10/1992 |
| JP | 6-345650 | 12/1994 |
| JP | 2003-70439 | 3/2003 |
| JP | 2003-212888 | 7/2003 |
| JP | 2004-500374 | 1/2004 |
| JP | 2004-530443 | 10/2004 |
| JP | 2005-179353 | 7/2005 |
| JP | 2005-224162 | 8/2005 |
| JP | 2006-81440 | 3/2006 |
| JP | 2007-7622 | 1/2007 |

*Primary Examiner* — Bernard Dentz
(74) *Attorney, Agent, or Firm* — Galbreath Law Offices, P.C.; John A. Galbreath (57) ABSTRACT

It is intended to provide a method for producing aglycone from a glycoside efficiently at low cost without using an acid catalyst or an organic solvent. The method for producing aglycone, characterized by bringing a glycoside into contact with high temperature high pressure water. The temperature of the high temperature high pressure water is generally from 100 to 374° C., preferably from 140 to 320° C., more preferably from 200 to 300° C. The pressure of the high temperature high pressure water may be not lower than the saturated water vapor pressure at the temperature, i.e., a pressure at which the liquid state is maintained.

5 Claims, 7 Drawing Sheets

METHOD FOR PRODUCING GLYCOSIDE AGLYCONE

BACKGROUND OF THE INVENTION

1. Field of the Invention

The present invention relates to a method for producing aglycone in which sugar residues are removed from a glycoside, particularly a method for producing aglycone from a glycoside efficiently at low cost without using an acid catalyst and an organic solvent.

2. Related Art

Many physiological active substances often have a structure in which naturally, sugar residues are bound to a matrix compound (hereinafter referred to as aglycone) composed of nonsugar moiety. It is said that presence of the sugar residues is purposed for stabilization, hydrophilicity, and detoxification. Therefore, physiological activities such as medical effect, antioxidance, and anticancer effect of the glycoside ordinarily exist in an aglycone region.

When orally administered, sugar residues of generally water-soluble glycoside are removed by intestinal bacteria and digestive enzymes, converting into aglycone which is easily absorbed into the intestinal tract. If aglycone is administered from the beginning, the increases in the intestinal absorption rate and the concentration in blood are expected.

As a method for extracting aglycone from a natural glycoside, conventionally-known methods are an enzyme reaction using glycosidase (Patent Documents 1 and 2) and an acid hydrolysis method (Patent Document 3). Further, Patent Document 4 describes a method that the aglycone freed by the above-described enzyme reaction and acid hydrolysis method is extracted into liquid in a subcritical state or supercritical state.

Patent Document 1: Japanese Unexamined Patent Publication No. 2006-081440
Patent Document 2: Japanese Unexamined Patent Publication No. 2005-224162
Patent Document 3: Japanese Unexamined Patent Publication No. H09-104693
Patent Document 4: Japanese Unexamined Patent Publication No. S63-33341

SUMMARY OF THE INVENTION

When the above-described enzyme reaction by glycosidase is industrially practiced, there are problems that costs of equipment and manufacturing are high, it requires reaction time and labor such as extraction, pH-adjustment, and enzyme removal, and the aglycone collection rate is low. With respect to the collection rate, a conversion rate from isoflavone glycoside to isoflavone aglycone is up to 94% and therefore pure aglycone is not obtained according to Patent Document 2. Further, the above-described enzyme reaction has problems of texture deterioration, smell occurrence, and others when it is produced as foods.

Meanwhile, strong acids such as hydrochloric acid and sulfuric acid used for an acid hydrolysis method cause corrosion of facilities. Furthermore, because glycoside and aglycone are hydrophobic and a hydrolysis reaction does not procede well in the presence of water, the acid hydrolysis method is required to carry out in an organic solvent. However, usage of chemicals such as a strong acid and an organic solvent is not preferable for consumers when the obtained aglycone is processed into foods. Emissions and wastes produced from a manufacturing process are not preferable for environment either. Further, the acid hydrolysis method is not efficient because it easily produces byproducts.

Therefore, it is an object of the present invention to provide a method for producing aglycone, which is friendly to humans and environment without using the above-described strong acids and organic solvents. Further object is to provide a method for producing aglycone from the glycoside form efficiently at low cost.

In deep consideration of the above-described objects, the inventors found that usage of high temperature high pressure water enables to produce aglycone efficiently without using acids and organic solvents, not as in conventional methods.

The present invention is characterized by bringing a glycoside into contact with high temperature high pressure water. In this specification, high temperature high pressure water means water having a temperature not higher than a critical point (374° C., 22.1 MPa) of water and a pressure not lower than a saturated vapor pressure at the temperature.

According to the present invention, the high temperature high pressure water has the following properties; (1) having characteristics similar to an organic solvent due to lowered dielectric constant of water, and dissolving the glycoside and aglycone, and (2) increasing ion product for water and having functions equal to more activated acid catalyst under high temperature. Utilizing these properties, only the sugar residues of the glycoside are hydrolyzed to free aglycone. Although the above-described Patent Document 4 describes that a liquid in a subcritical state is used, it is used only for extracting freed aglycone. Therefore, Patent Document 4 is different from the present invention in the method for producing aglycone.

Almost all organic compounds are decomposed in a hydrothermal reaction using supercritical water. However, according to the production method of the present invention, only the sugar residues are efficiently removed by properly adjusting conditions of high temperature high pressure water, so that the aglycone can be obtained as it is.

The present invention further provides an aglycone which is obtained by the above-described production method and a purity degree with respect to aglycone is from 95 to 100%. Here, "a purity degree with respect to aglycone" means a ratio of weight of the aglycone to total weight of freed aglycone and aglycone in unreacted glycoside.

According to the production method of the present invention, reaction elements are only sample and water, and there is no need to use organic solvent, acid catalyst, enzyme, and others, not as in conventional methods. Therefore, there is no need to wash and remove a residual catalyst and a residual enzyme, nor need to pH-adjust an acid catalyst. Further, the production method of the present invention is also advantageous in respect that a rate of conversion into aglycone is higher than that of an enzyme reaction. Further, according to the production method of the present invention, when high temperature high pressure water is returned back to ordinary water after the treatment, aglycone is easily separated from the water because water-insoluble aglycone deposits in a water layer. Therefore, according to the production method of the present invention, separation of aglycone and sugar residues becomes very simple compared with the conventional method.

Since an aglycone conversion rate according to the production method of the present invention is high, a purity degree of aglycone is elevated compared with aglycone obtained by the conventional method. In other words, according to the present invention, high-purity aglycone is provided.

DESCRIPTION OF THE PREFERRED EMBODIMENTS

Hereinafter, a method for producing aglycone of the present invention is explained with reference to one embodiment. First, glycoside which can be applied to the present invention includes all glycosides compounds made by a reaction of dehydration and condensation between a hemiacetal hydroxyl group or a hemiketal hydroxyl group in sugar residues and a reaction group in alcohol, phenol, carboxylic acid, etc. Although the glycoside is principally a natural secondary metabolite, it also includes chemically synthesized compounds having the same structure.

The above-described glycoside is classified into O-glycoside, S-glycoside, N-glycoside, and C-glycoside according to types of atomic bound with sugar residues. The production method of the present invention does not depend on types of atomics to be bound to and is applicable to all glycosides.

Examples of a structure of aglycone of the above-described glycoside include flavonoids including isoflavone, flavanone, flavone, flavan, chalcone, dihydroxychalcone, catechin, flavanol, neoflavanoid, flavonole, aurone, anthocyanin, and leucoanthocyan; terpenoids including saponigen; steroids including digoxigenin, digitoxigenin, uzarigenin, strophanthidin, gitoxigenin, acetylstrophanthidin, and ouabagenin; quinones; and lignans.

On the other hand, specific examples of the sugar residues existing in the glycoside include monosaccharide including glucose, mannose, galactose, fucose, rhamnose, arabinose, xylose, fluctose, and digitoxose; disaccharide including maltose, sucrose, and lactose; and oligosaccharide bound with three to eight pieces of the above-described sugar.

Specific examples of glycosides of an O-glycoside type naturally existing include isoflavone, saponin, oleuropein, anthocyanin, rutin, apiin, hesperidin, naringin, citronine, tricine, sennoside, bufotoxin, digitoxin, lantoside C, deslanoside, digoxin, methyldigoxin, ouabain, G-strophanthin, amygdalin, stevioside, glycyrrhizin, swertiamarin, and gentiopicroside.

The above-described isoflavone is one type of flavonoid glycosides which are much contained in plants of rosaceae, iridaceae, moraceae, and amaranthaceae, and leguminous plants such as soybean, pea, chickpea, clover, gorse, and kudzu. With respect to soybean isoflavone, glycosides such as daidzin, glycitin, and genistin are confirmed.

Chemical structure formulas of daidzin and daidzein being aglycone thereof are shown below.

Daidzin

Daidzein

[Where $R_1$, $R_2$, $R_3$, $R'_1$, and $R'_2$ represent hydrogen atoms.]

The above-described saponin is an amorphous glycoside which abundantly exists in soybean, red bean, olive, and others.

There are two types of saponin depending on types of aglycone; triterpenoid saponin and steroid saponin. Aglycone of the triterpenoid saponin is oleanane or dammarane. On the other hand, aglycone of the steroid saponin is spirostane, furostane, or $C_{27}$-steroid alkaloid.

Chemical structure formulas of soybean saponin B glycoside being a type of triterpenoid saponin and soyasapogenol B being aglycone thereof are shown below.

Soyasaponin B

Soyasapogenol B

[Where $R_1$ represents $CH_2OH$ or hydrogen atom, and $R_2$ represents β-Glc, α-L-Rha or hydrogen atom.]

The above-described oleuropein is obtained by extracting principally with water and/or organic solvent from fruit, seed, fruit skin, seed skin, leaf, stem, and bud of olive, or these which are dried, ground, or defatted. The chemical structure formula is shown below.

(Where "Glucose" Expresses Glucose.)

Further, rutin is a flavonoid glycoside which is contained in buckwheat and tea leaves. Digitoxin is colorless white-crystalline powder which is contained in digitalis. Lanatoside C is much contained in digitalis lanata. Lanatoside C is hydrolyzed with alkali to obtain deslanoside. Deslanoside is removed of glucose by an enzyme reaction to obtain digoxin. Strophanthin is a glycoside contained in apocynaceae plants. Glycyrrhizin and glycyrrhizard are colorless crystal contained in licorice roots. Amygdalin is much contained in bitter almond and fruit nucleus. Arbutin exists in rhododendron plants, and plants such as cowberry and uva-ursi.

An example of glycoside of S-glycoside type which exists in nature is sinigrin. Sinigrin exists in vegetable leaf, seed, and root of cruciferous plants such as black mustard, horseradish, leaf mustard, radish, and watercress.

An example of glycoside of C-glycoside type which exists in nature is aloin, mangiferin, and aloesin. Aloin exists in leaves of aloe plants.

The above-described glycoside is subject to a high temperature high pressure water treatment as a uniform water solution or a suspension liquid. Here, a solid glycoside may be broken up and then dissolved or suspended in water.

A concentration of the glycoside used as an ingredient may be in such that it is dissolved in water or in a suspension state for maintaining fluidity. Ordinarily, it is from 1 to 50% (w/w), preferably from 5 to 20% (w/w).

A temperature of the high temperature high pressure water is from 100 to 374° C., preferably from 140 to 320° C., more preferably from 200 to 300° C. Its pressure may be not lower than a saturated water vapor pressure corresponding to the above-described temperature, in other words a pressure at which the liquid state is maintained. Preferably, the pressure is higher by a range of 0 to 22 MPa than the saturated water vapor pressure corresponding to the above-described temperature. More preferably the pressure is the saturated water vapor pressure corresponding to the above-described temperature. When the treatment temperature and pressure are easier than the above-described range, the hydrolysis reaction of the glycoside does not proceed so that a collection rate of aglycone does not increase. On the contrary, when they are harder than the above-described range, the thermal decomposition reaction proceeds so that a collection rate of aglycone decreases. Further, there also occur problems that a reaction apparatus becomes corrosive and higher pressure resistance is required.

Since appropriate conditions of the high temperature high pressure water vary depending on properties of glycoside, they are adjusted accordingly. For example, the temperature of the high temperature high pressure water treatment of soybean saponin is preferably from 240 to 320° C. under the saturated water vapor pressure, more preferably from 240 to 280° C. The temperature of the high temperature high pressure water treatment of soybean isoflavone is preferably from 200 to 320° C., more preferably from 240 to 280° C.

Time of contact between the glycoside and the high temperature high pressure water may be ordinarily from 0.1 to 120 minutes, preferably from 0.5 to 20 minutes, more preferably from 1 to 5 minutes, furthermore preferably from 1 to 3 minutes. In the case of excessively short contact time, the hydrolysis reaction does not proceed and the glycoside remains in the product. On the contrary, in the case of excessively long contact time, the hydrolysis and thermal decomposition of aglycone proceed and the collection rate of the aglycone decreases.

Detail of the contact time is appropriately adjusted depending on treated glycoside properties, temperature and pressure. For example, in the case of glycosides of soybean isoflavone and soybean saponin, when the reaction is caused for 1 to 5 minutes at a temperature of 240 to 280° C. and a saturated vapor pressure of the temperature, it is possible to decompose and remove only sugar residues and leave aglycone.

According to the production method of the present invention, when glycosides are treated with the high temperature high pressure water, those having a water phase and a solid phase which are separated are obtained. Aglycone is included in the solid phase and sugar which had been bound to the glycoside is included in the water phase.

The aglycone in the solid phase becomes gel state or deposit depending on a condition of the high temperature high pressure water. Preferably, a condition of high temperature and high pressure water that deposit is obtainable is employed. A method for separating the deposit is not specifically limited. Natural deposition, centrifugal separation, and filtration are included. The centrifugal separation is preferable. In the case of a rigid gel state, it may be evaporated and dried and subsequently washed to remove water soluble components.

According to the production method of the present invention, a conversion rate from the glycoside to the aglycone (collection rate of aglycone) reaches 70 to 100% by adjusting conditions, preferably 95 to 100%, further more preferably 99 to 100%. Therefore, the present invention also provides aglycone in which a purity degree with respect to the aglycone obtained by the above-described production method, is ordinarily 70 to 100%, preferably 95 to 100%, further more preferably 99 to 100%.

In the case where impurities are included in the collected aglycone, it may be refined according to ordinary methods. For example, solvent fractionation, column chromatography, distillation, and membrane separation are included.

Further, the sugar included in the above-described water phase after the high temperature high pressure water treatment may be separated and refined according to ordinary methods. Specifically, ion exchange, adsorption, distillation, evaporation, salting-out, membrane separation, and extraction are included.

The high temperature high pressure water treatment apparatus employed in the production method of the present invention is not specifically limited. For example, well-known high temperature high pressure water treatment apparatuses of batch type and continuous type may be employed.

Figure 1:
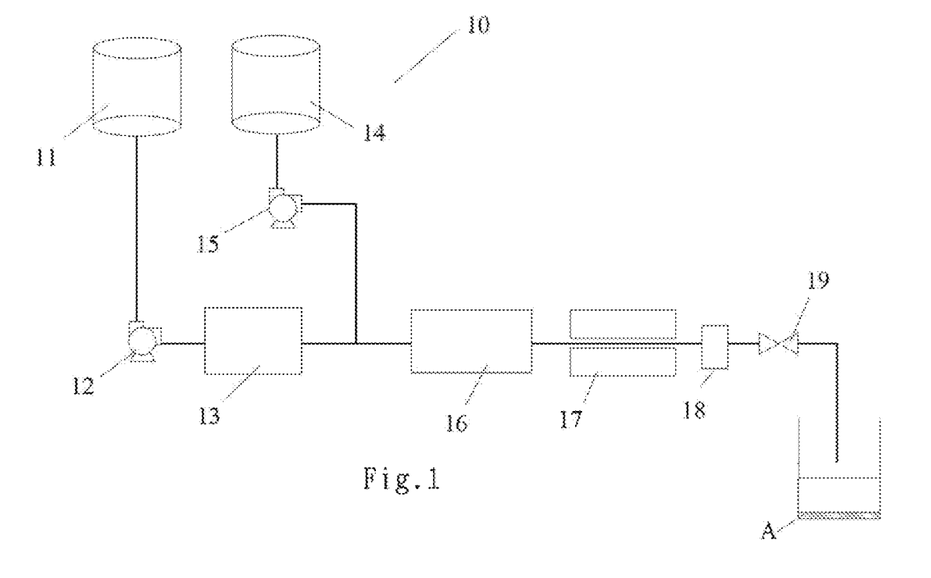
FIG. 1 is a schematic view showing a continuous reaction system for practicing a method for producing aglycone according to the present invention.

FIG. 1 shows a reaction system for producing aglycone using a continuous-type high temperature high pressure water treatment apparatus. After being pressure-raised into a predetermined pressure by a water pump 12, water in a water tank 11 is heated by a heater 13 to produce hot water having a predetermined temperature. A glycoside as an ingredient is mixed with water and formed into a state of solution or slurry liquid, and subsequently fed into an ingredient tank 14. Next, the ingredient is pressure-raised by a slurry pump 15, and ingredient slurry is mixed with hot water and passed through a high temperature high pressure water reaction heat/pressure resistant pipe 16. Subsequently, it is cooled into a room temperature by a cooler 17, undissolved solid part is removed by a filter 18, and treated water is collected into a container through a back pressure valve 19. Because the aglycone becomes insoluble in water when it is returned into an ordinary pressure, it deposits much in the container. In this case, the deposit is collected as aglycone.

Figure 2:
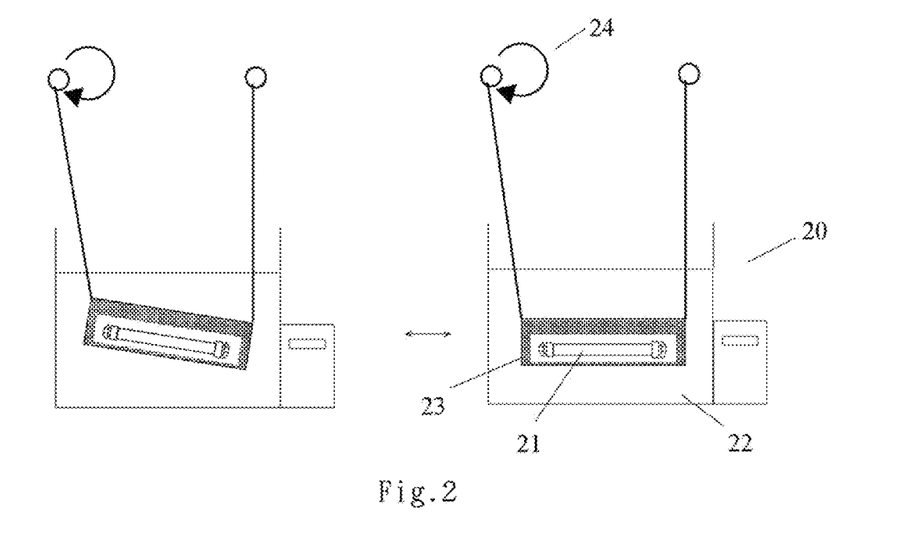
FIG. 2 is a schematic view showing a batch-type reaction apparatus for practicing the method for producing aglycone according to the present invention.

A batch-type apparatus for producing aglycone comprises: as shown in for example FIG. 2, a pressure/heat resistant pipe 21 which is openable and closable and made of corrosion-resistant material such as stainless steal; a constant-temperature apparatus such as a salt bath 22 at a temperature of high temperature high pressure water; and a mechanism for uniforming contents of the reaction container such as an agitator 24 and a reaction pipe oscillation apparatus. The reaction pipe is contained with the glycoside and water and closed, and heated to a predetermined temperature. When temperature and pressure inside the reaction pipe become high, water inside the reaction pipe becomes high temperature high pressure water and aglycone is freed by hydrolysis reaction.

EXAMPLES

Hereinafter, although the present invention is explained in more detail by giving examples, it is not limited thereto.

Examples 1 to 6 and Comparison Examples 1 to 2

Production of Soybean Saponin Aglycone from Soybean Saponin

[Preparation of Reaction Pipe]

A batch-type reaction apparatus 20 shown in FIG. 2 is used for a high temperature high pressure water treatment. This reaction apparatus 20 has caps (product name: SS-600-C, manufactured by SWAGELOK) which are removably fit to both ends of a stainless steal pipe 21 (outer diameter: 10 mm, inner diameter: 8.2 mm, length: 150 mm, capacity: 8.2 cm$^3$).

[Preparation of Salt Bath]

A salt bath 22 (product name: Thermometer Inspecting Bath CELSIUS600H, manufactured by Thomas Kagaku Co., Ltd.) is used for keeping high temperature of the reaction pipe 21 constant during the high temperature high pressure water treatment. For a heat medium inside the salt bath, mixed salt (melting point: 140° C.) having potassium nitrate and sodium nitrite which are mixed at a rate of 1:1 is used. The reaction apparatus 20 further has a basket (height: 7 cm, width: 20 cm, depth: 3 cm) for keeping the reaction pipe and an agitator 24 for agitating samples inside the reaction pipe by vertically swinging the basket.

[Calculation of Pressure in Respective Treatment Temperature and Water Preparation Amount]

A pressure inside the reaction pipe is assumed equal to a saturated vapor pressure of water. A ratio of respective phases to a capacity inside the pipe is expressed by the following formula:

$$V = V_s + V_1 + V_2 \quad (1)$$

[Where V represents reaction pipe capacity (cm³), $V_s$ is (dried) glycoside volume (cm³), $V_1$ is water phase (liquid phase) volume (cm³), $V_2$ is gas phase volume (cm³).]

Further, relation between a (dried) glycoside preparation amount (g) and a water preparation amount is expressed by the following formula:

$$m_w + m \times w = V_1/v_1 + V_2/(v_2 \times \rho) \quad (2)$$

[Where V, $V_s$, $V_1$ and $V_2$ are same as the above description. $m_w$ represents water preparation amount (g), m is (dried) glycoside weight (g), w is water content rate, $v_1$ is specific water capacity in water phase (cm³/g), $v_2$ is specific water capacity in gas phase (cm³/g), $\rho$ is water density (g/cm³).]

In the case of glycoside 0, a water preparation amount V which is allowed to be fed in the reaction pipe is:

$$V_1 = V = 8.2 \text{ g}$$

Therefore, the amount of the water is $8.2/v_1$ (g) in a reaction pipe capacity at a temperature of a high temperature high pressure water treatment. A maximum water phase amount is 80% thereof for allowing a portion of gas phase. Table 1 shows a specific capacity of the saturated vapor pressure and water and a specific capacity of the water vapor at a temperature of the high temperature high pressure treatment used in an experiment.

TABLE 1

| Temperature (° C.) | Saturated vapor pressure (kg/cm²) | (Mpa) | Specific water capacity $v_1$ (cm³/g) | Specific water vapor capacity $N_2$ (cm³/g) |
|---|---|---|---|---|
| 200 | 15.855 | 1.5548444 | 1.15649 | 127.16000 |
| 240 | 34.138 | 3.3477942 | 1.22978 | 59.65440 |
| 280 | 65.468 | 6.4202176 | 1.33239 | 30.12600 |
| 320 | 115.120 | 11.2894155 | 1.49950 | 15.47980 |
| 360 | 190.430 | 18.6748036 | 1.89590 | 6.93980 |

[Sample Feeding]

Figure 3:
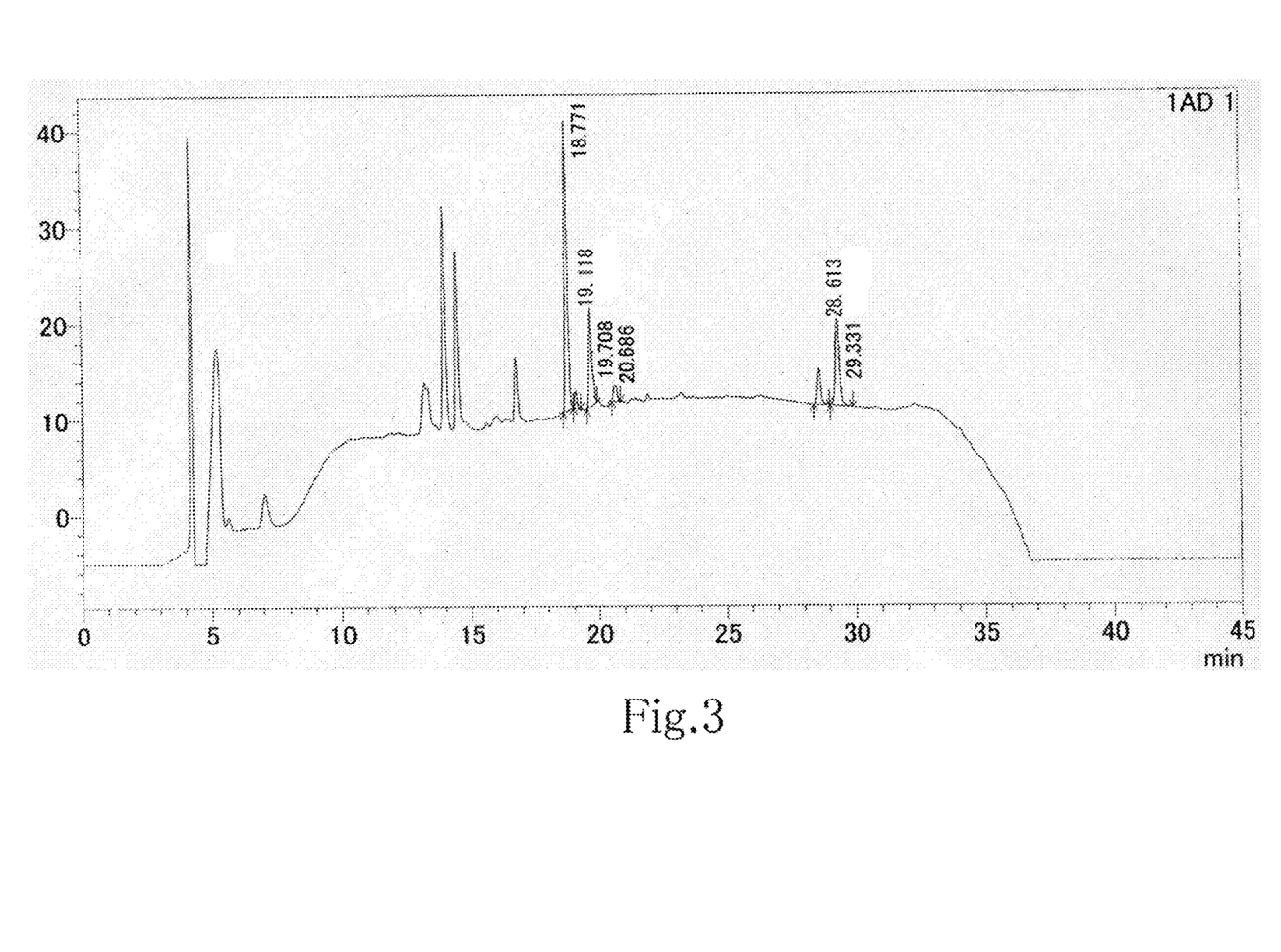
FIG. 3 is a chromatogram of a soybean saponin glycoside used in Examples 1 to 6. Here, an X-axis represents elution time (minute) and a Y-axis represents absorbancy (relative value).

A glycoside sample solution is prepared by adding water of 19 weight parts to a soybean saponin concentrate (glycoside concentration of 80%) of 1 weight part, which is extracted from hypocotyls of soybean (Glycine max) according to a solvent extraction method described in Japanese Unexamined Patent Publication No. 2006-124324. A chromatogram of the soybean saponin glycoside is shown in FIG. 3. Analysis conditions of the soybean saponin glycoside are described below.

Column: ODS column (SHISEIDO CAPCELL PAK C18 AG-120 Size 4.6×250 nm)
Mobile phase:
A liquid: Water:TFA=100:0.05 (v/v)
B liquid: Acetonitrile:TFA=100:0.05 (v/v)
Flow rate: 0.7 mL/min
Column temperature: 40° C.
Detection: 205 nm (UV detector)
Injection volume: 10 μL
Elution conditions:
Linear gradient is carried out:
0 minute: B liquid ratio of 13%,
0 to 10 minutes: B liquid ratio of 13 to 30%,
10 to 20 minutes: B liquid ratio of 30 to 50%,
20 to 25 minutes: B liquid ratio of 50 to 50%,
25 to 35 minutes: B liquid ratio of 50 to 100%,
35 to 55 minutes: B liquid ratio of 100 to 100%,
55 to 57 minutes: B liquid ratio of 100 to 13%, and
57 to 65 minutes: B liquid ratio of 13 to 13%.

Soyasaponin A1 (elution time: 18.771 minutes) is detected with respect to soybean saponin A glycoside, and soyasaponin I (elution time: 29.331 minutes) and soyasaponin V (elution time: 28.613 minutes) are detected with respect to soybean saponin B glycoside.

This sample solution of approximately 3.46 g is split and filled in the above-described reaction pipe 21, and the reaction pipe is capped.

[High Temperature High Pressure Water Treatment]

After the reaction pipe 21 thus filled with the glycoside and the water is placed in a basket 23, the reaction pipe 21 with the basket 23 as a whole is submerged in a salt bath 22 at temperatures shown in Table 2 below.

During the high temperature high pressure water treatment (1 or 5 minutes), the reaction pipe 21 is vertically swung with the above-described agitator 24 at intervals of 35 times/min. Subsequently, the above-described reaction pipe 21 is drawn out from the salt bath 22 and cooled with water.

[Collection of Water Phase and Deposit]

Thus water-cooled reaction pipe 21 is shaken well to uniform the contents. The cap of the reaction pipe 21 is opened, whole amount of the contents of the pipe is transferred to a test tube with a push stick having a chip made by Viton. Water is added to the test tube to make a capacity approximately 10 ml.

Subsequently it is spun down by centrifugal treatment (4000 rpm×15 minutes). After spinning down, a result of state observation is described in Table 2.

[Ethanol Treatment of the Deposit]

Whole amount of the spun contents inside the test tube is subject to decantation, filtered, and washed. The water phase is discarded. On the other hand, a solid on a filter paper is dissolved with ethanol, thus the obtained ethanol solution is again filtered. A solid finally left on the filter paper is to be an insoluble matter.

Thus filtered ethanol solution is transferred to the test tube. A state observation result of the ethanol solution is shown in Table 2. Contents of the ethanol solution are identified with high-performance liquid chromatography (manufactured by Shimadzu Corporation). The analysis conditions of the soybean saponin aglycone are described below.

Column: ODS column (SHISEIDO CAPCELL PAK C18 AG-120 Size 4.6×250 nm)
Mobile phase: Acetonitrile:Water:1-propanol:0.01% acetic acid=80:13.9:6:0.1 (V/V/V/V)
Flow rate: 0.9 mL/min
Column temperature: 40° C.
Detection: 205 nm (UV detector)

Injection volume: 20 μL

Figure 4:
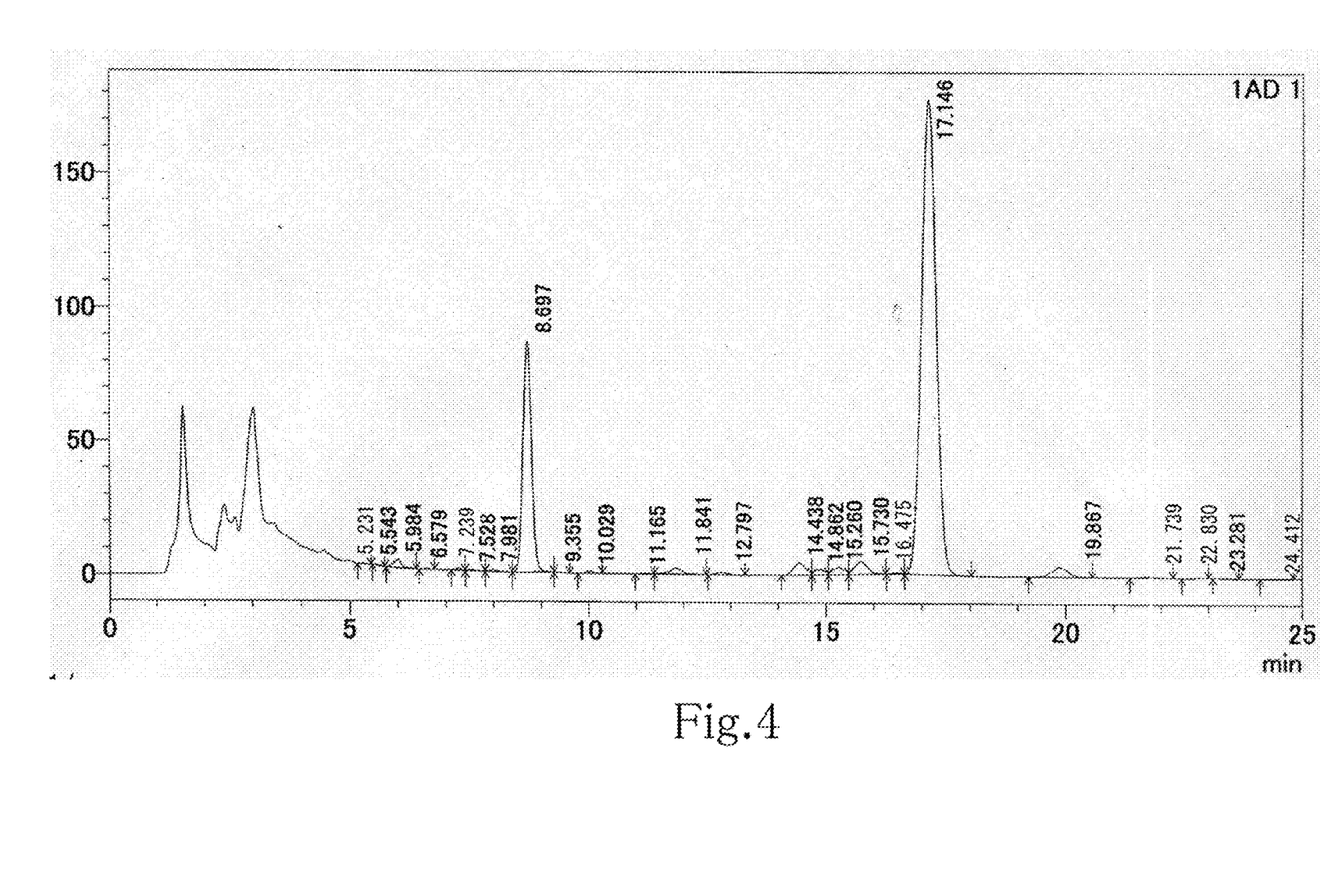
FIG. 4 is a chromatogram of a soybean saponin aglycone used in Examples 1 to 6. Here, an X-axis represents elution time (minute) and a Y-axis represents absorbancy (relative value).

As soyasapogenole A (elution time: 8.697 minutes) and soyasapogenole B (elution time: 17.146 minutes) are detected in the chromatogram of FIG. 4, it is confirmed that soybean saponin aglycone is much contained.

TABLE 2

| | Temperature (° C.) | Contact time (min.) | State of centrifugal deposit treatment | Visual observation state of ethanol solution |
|---|---|---|---|---|
| Example 1 | 240 | 1 | Yellow supernatant + gel state deposit | — |
| Example 2 | 240 | 5 | Orange color supernatant + powder state deposit | Blackish brown liquid |
| Example 3 | 280 | 1 | Orange color supernatant + powder state deposit | Blackish brown liquid |
| Example 4 | 280 | 5 | Orange color supernatant + powder state deposit | Blackish brown liquid |
| Example 5 | 320 | 1 | Orange color supernatant + powder state deposit | Blackish brown liquid |
| Example 6 | 360 | 1 | Orange color supernatant + powder state deposit | Blackish brown liquid |

TABLE 2-continued

| | Temperature (° C.) | Contact time (min.) | State of centrifugal deposit treatment | Visual observation state of ethanol solution |
|---|---|---|---|---|
| Comparison Example 1 | 200 | 1 | Completely white gel | — |
| Comparison Example 2 | 200 | 5 | Completely brown gel | — |

[Collection Rate, Concentration, and Concentration Rate of Aglycone]

Gel of Example 1 is evaporated and dried, and collection amount is measured by weight. Further, the amount of collected aglycone is determined by the high-performance liquid chromatography (manufactured by Shimadzu Corporation). Products of Examples 2 to 6 are distilled away by mixing an ethanol solution and a deposit dissolution substance, and subsequently the collection amount is measured by weight. Further, the amount of collected aglycone is determined by the high-performance chromatography (manufactured by Shimadzu Corporation). In Comparison examples 1 and 2, the gel is intended to evaporate and dry, and measure by weight as in Example 1. However, soybean saponin aglycone can not be obtained.

Table 3 shows the collected aglycone amount, aglycone collection rate, aglycone concentration, and concentration rate. The aglycone collection rate reaches nearly 100% with Example 2 (240° C.×5 minutes) and Example 3 (280° C.×1 minute). Mole number of the collected aglycone to mole number of ingredient glycoside is nearly 100%. Therefore, it is estimated that a transform rate from the glycoside to the aglycone is also nearly 100%.

Figure 8:
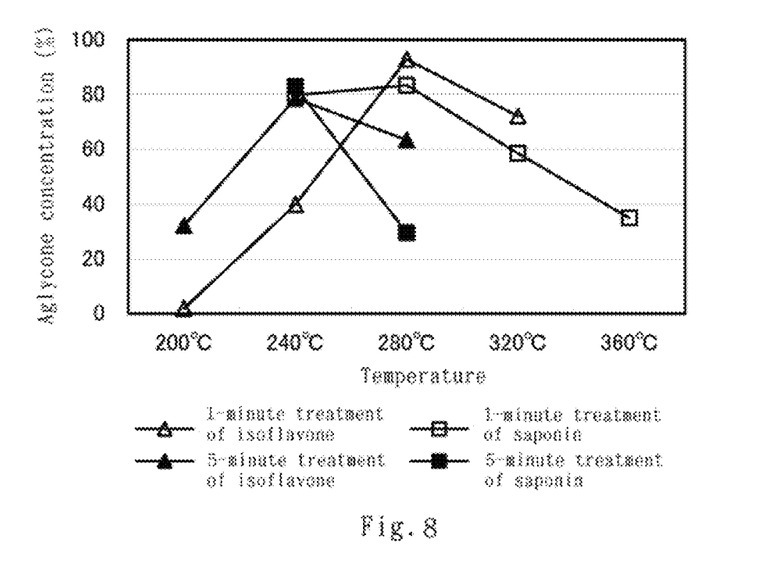
FIG. 8 shows concentrations of a soybean saponin aglycone and a soybean isoflavone aglycone in the obtained product, which are produced according to the production method of the present invention.
Figure 9:
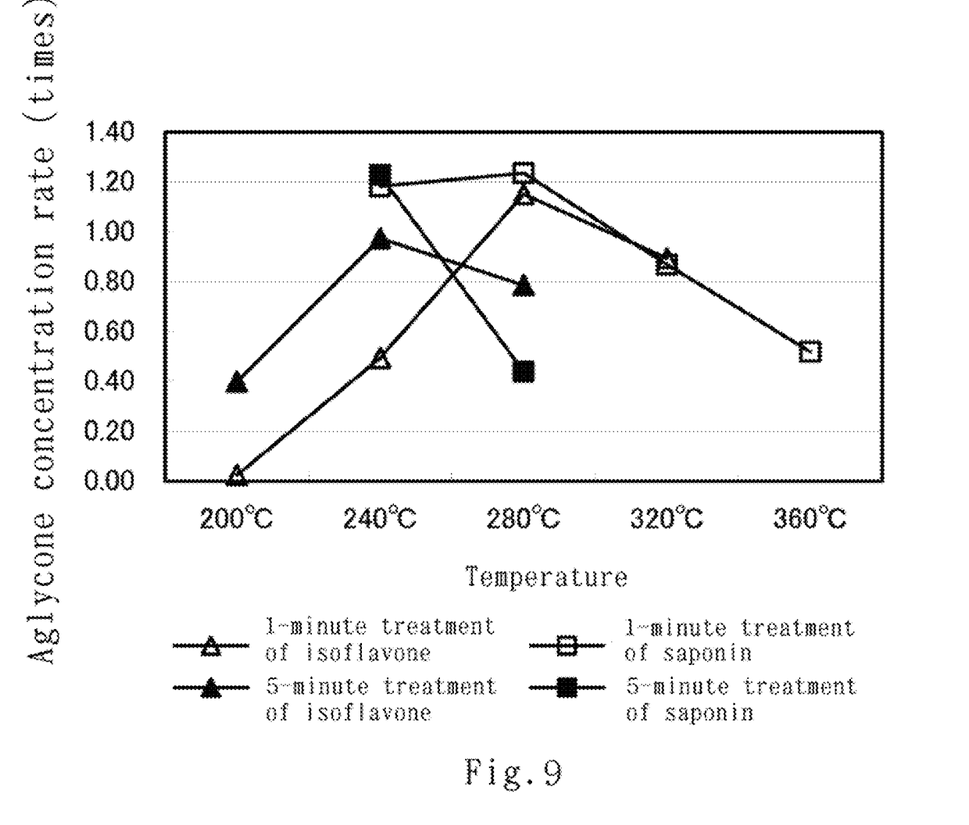
FIG. 9 shows concentration rates of a soybean saponin aglycone and soybean isoflavone aglycone compared to glycosides (at a preparation time), which are produced according to the production method of the present invention.

With respect to the aglycone concentration and the concentration rate, on conditions of Example 1 (240° C.×1 minute), Example 2 (240° C.×5 minutes), and Example 3 (280° C.×1 minute), the concentration is higher than a glycoside concentration (67.5%) in the sample solution. Besides, the aglycone concentration becomes maximum on the conditions of Examples 2 and 3 (FIGS. 8 and 9).

TABLE 3

| | Glycoside preparation amount (g) | Collected aglycone amount (g) | Aglycone collection rate[1] (%) | Collected aglycone concentration[2] (%) | Concentration rate[3] (times) |
|---|---|---|---|---|---|
| Example 1 | 0.1229 | 0.0339 | 73.5 | 79.8 | 1.18 |
| Example 2 | 0.1208 | 0.0539 | 100 | 82.9 | 1.23 |
| Example 3 | 0.1208 | 0.0550 | 100 | 83.4 | 1.24 |
| Example 4 | 0.1208 | 0.0031 | 42.4 | 29.6 | 0.44 |
| Example 5 | 0.1229 | 0.0434 | 78.8 | 58.6 | 0.87 |
| Example 6 | 0.3809 | 0.0900 | 52.8 | 52.8 | 0.52 |
| Comparison Example 1 | 0.1225 | 0 | 0 | 0 | — |
| Comparison Example 2 | 0.1486 | 0 | 0 | 0 | — |

[1]Aglycone collection rate = Collected aglycone amount/Aglycone amount in prepared glycoside
[2]Collected aglycone concentration = Collected aglycone amount/Total amount of collection
[3]Concentration rate = Collected aglycone concentration/Glycoside concentration in sample solution Examples 7 to 13

Production of Soybean Isoflavone Aglycone

[Sample Feeding]

Figure 5:
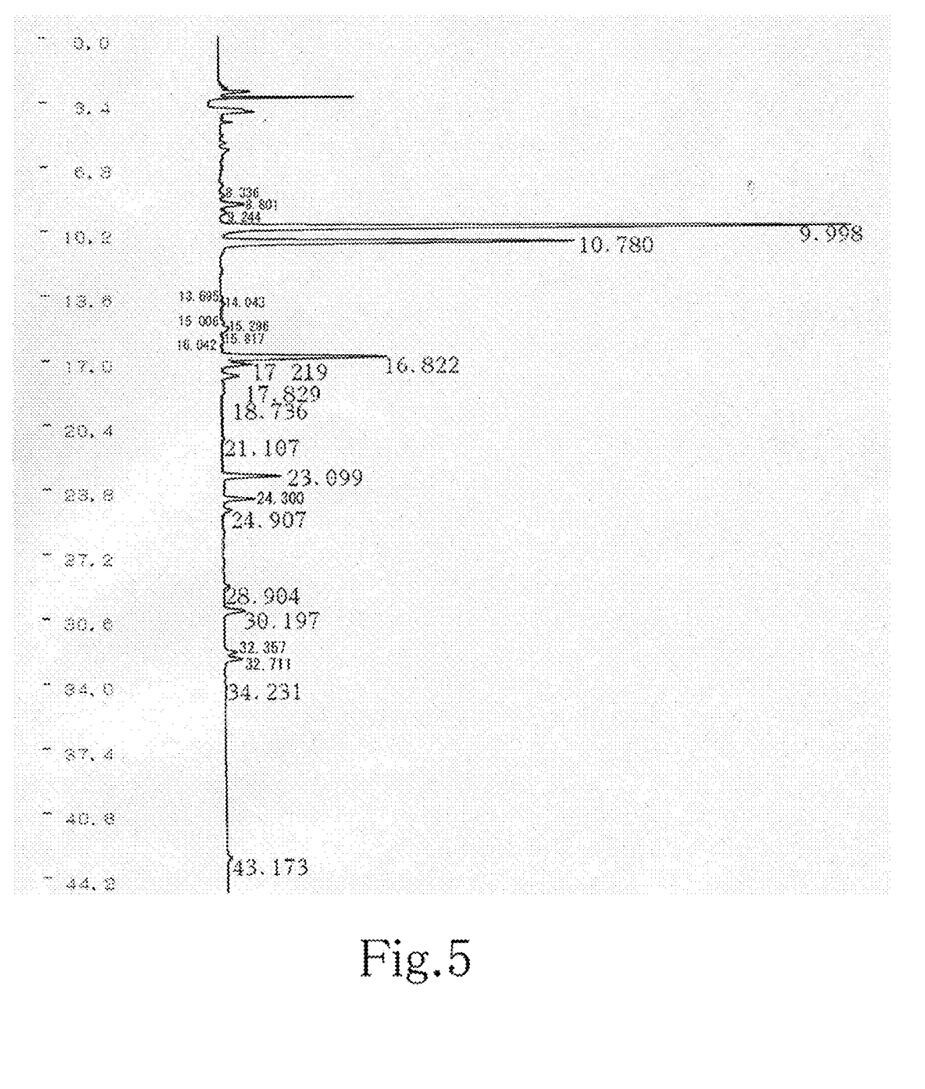
FIG. 5 is a chromatogram of a soybean isoflavone glycoside used in Examples 7 to 13. Here, an X-axis represents absorbancy (relative value) and a Y-axis represents elution time (minute).

A sample solution is prepared by adding water of 18 weight parts to a soybean isoflavone concentrate (glycoside concentration of 80%) of 1 weight part, which is extracted from hypocotyls of soybean (Glycine max). A chromatogram of the soybean isoflavone glycoside is shown in FIG. 5. Analysis conditions of the soybean isoflavone glycoside are described below.

Column: ODS column (YMC-pack ODS-AM-303 Size 4.6× 250 nm)
Mobile phase:
A liquid: Acetonitrile:Water:Acetic acid=15:85:0.1 (v/v)
B liquid: Acetonitrile:Water:Acetic acid=35:65:0.1 (v/v)
Flow rate: 1.0 mL/min
Column temperature: 40° C.
Detection: 254 nm (UV detector)
Injection volume: 10 μL Elution conditions:
Linear gradient is carried out:
0 minute: B liquid ratio of 0%,
0 to 50 minutes: B liquid ratio of 0 to 100%,
50 to 55 minutes: B liquid ratio 100 to 0%, and
55 to 60 minutes: B liquid ratio of 0 to 0%.

Among soybean isoflavone glycoside, daidzin (elution time: 9.998 minutes), glycitin (elution time: 10.780 minutes) and genistin (elution time: 16.822 minutes) are detected.

This sample solution of approximately 3.46 g is split and filled in the reaction pipe 21 as in Example 1.

[High Temperature High Pressure Water Treatment]

After the reaction pipe 21 filled with the glycoside and the water is placed in a basket 23, the reaction pipe 21 with the basket 23 as a whole is submerged in the salt bath 22 at temperatures shown in the table below. During the high temperature high pressure water treatment (1 or 5 minutes), the reaction pipe 21 is vertically swung with the above-described agitator 24 at intervals of 35 times/min. Subsequently, the above-described reaction pipe is drawn out from the salt bath 22 and cooled with water.

[Collection of Water Phase and Deposit]

The water-cooled reaction pipe 21 is shaken well to uniform the contents. The cap of the reaction pipe 21 is opened, whole amount of the contents of the pipe is transferred to the test tube with the push stick having a chip made by Viton. Water is added to the test tube to make a capacity approximately 10 ml. Subsequently it is spun down by centrifugal treatment (4000 rpm×15 minutes). After spinning down, a result of state observation is described in Table 4.

[Ethanol Treatment of the Deposit]

Whole amount of the spun contents inside the test tube is subject to decantation, filtered, and washed. After a head space is argon-substituted, the water phase is cooled and preserved. On the other hand, a solid on a filter paper is dissolved with ethanol, thus obtained ethanol solution is again filtered. A solid finally left on the filter paper is to be an insoluble matter.

Thus filtered ethanol solution is transferred to the test tube. A state observation result of the ethanol solution is shown in Table 4. Contents of the ethanol solution are identified with high-performance liquid chromatography. The analysis conditions of the soybean isoflavone aglycone are described below.

Column: ODS column (YMC-pack ODS-AM-303 Size 4.6× 250 nm)
Mobile phase:
A liquid: Acetonitrile:Water:Acetic acid=15:85:0.1 (v/v)
B liquid: Acetonitrile:Water:Acetic acid=35:65:0.1 (v/v)
Flow rate: 1.0 mL/min
Column temperature: 40° C.
Detection: 254 nm (UV detector)
Injection volume: 10 μL Elution conditions:
Linear gradient is carried out:
0 minute: B liquid ratio of 0%,
0 to 50 minutes: B liquid ratio of 0 to 100%,
50 to 55 minutes: B liquid ratio 100 to 0%, and
55 to 60 minutes: B liquid ratio of 0 to 0%.

Figure 6:
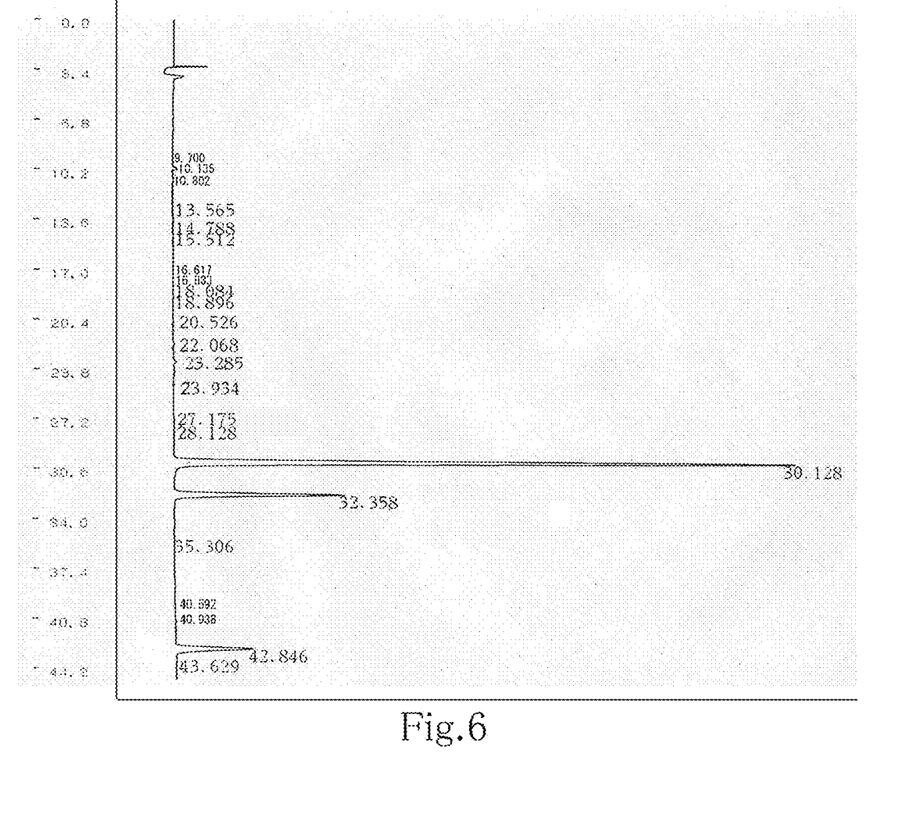
FIG. 6 is a chromatogram of a soybean isoflavone aglycone used in Examples 7 to 13. Here, an X-axis represents absorbancy (relative value) and a Y-axis represents elution time (minute).

As daidzein (elution time: 30.128 minutes), glycitein (elution time: 32.358 minutes) and genistein (elution time: 42.846 minutes) are detected as soybean isoflavone aglycone in the chromatogram of FIG. 6, it is confirmed that soybean isoflavone aglycone is much contained.

TABLE 4

| | Temperature (° C.) | Contact time (min.) | State of product | State of ethanol solution of deposit |
|---|---|---|---|---|
| Example 7 | 200 | 1 | Colorless supernatant + powder state deposit | Light purple liquid |
| Example 8 | 200 | 5 | Colorless supernatant + powder state deposit | Light brown liquid |
| Example 9 | 240 | 1 | Colorless supernatant + powder state deposit | Nearly colorless liquid |
| Example 10 | 240 | 5 | Yellow supernatant + powder state deposit | Yellowish brown liquid |
| Example 11 | 280 | 1 | Yellow supernatant + powder state deposit | Yellowish brown liquid |
| Example 12 | 280 | 5 | Yellow supernatant + powder state deposit | Brown liquid |
| Example 13 | 320 | 1 | Yellow supernatant + powder state deposit | Brown liquid |

[Derivation of Collection Rate, Concentration, and Concentration Rate of Aglycone]

In products of Examples 7 to 13, ethanol solution and deposit dissolved matter are solvent-distilled away, and the collection amount is measured by weight. Further the amount of collected aglycone is determined by the high-performance liquid chromatography (manufactured by Shimadzu Corporation). The results are shown in Table 5 together with collection rate, concentration, and concentration rate of aglycone.

TABLE 5

| | Glycoside preparation amount (g) | Collected aglycone amount (g) | Aglycone collection rate (%) | Collected aglycone concentration (%) | Concentration rate (times) |
|---|---|---|---|---|---|
| Example 7 | 0.1558 | 0.0092 | 2.5 | 2.0 | 0.02 |
| Example 8 | 0.1566 | 0.1402 | 38.5 | 32.2 | 0.40 |
| Example 9 | 0.1574 | 0.1709 | 46.4 | 39.8 | 0.49 |
| Example 10 | 0.1590 | 0.2109 | 56.7 | 78.6 | 0.97 |
| Example 11 | 0.1558 | 0.3547 | 97.3 | 92.9 | 1.15 |
| Example 12 | 0.1574 | 0.2538 | 68.9 | 63.4 | 0.79 |
| Example 13 | 0.1574 | 0.2599 | 70.6 | 72.1 | 0.89 |

Figure 7:
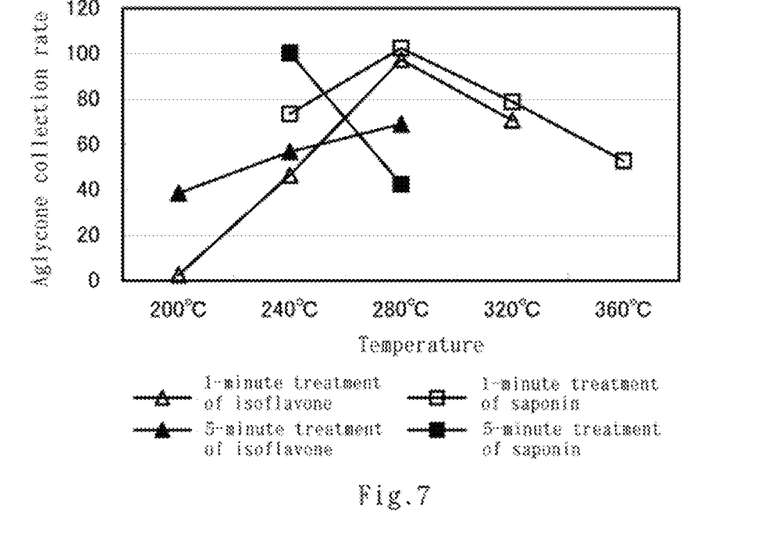
FIG. 7 shows collection rates of a soybean saponin aglycone and a soybean isoflavone aglycone which are produced according to the production method of the present invention.

The aglycone collection rate reaches nearly 100% on conditions of Example 11 (280° C.×1 minute). On the condition of Example 11 (280° C.×1 minute), the aglycone collection rate is concentrated more than an initial concentration (80.7%) in the glycoside and aglycone concentration becomes maximum (FIGS. 7 to 9).

Example 14

Sample Feeding

A sample solution is prepared by dispersing an olive extract (product name: "OPIACE") which contains oleuropein of approximately 35% or more, in water at a concentration of approximately 5%. Approximately 3.6 g is split from this sample solution in uniform state and filled in the reaction pipe 21 similar to Example 1.
(High Temperature High Pressure Water Treatment and Collection Rate Measurement)

After the reaction pipe 21 filled with glycoside and water is placed in the basket 23, the reaction pipe 21 with the basket 23 as a whole is submerged in the salt bath 22 at temperatures shown in Table below. During the high temperature high pressure water treatment (1 minute, 5 minutes), the reaction pipe 21 is vertically swung with the above-described agitator 24 at intervals of 35 times/min. Subsequently, the above-described reaction pipe is drawn out from the salt bath 22 and cooled with water.

The obtained sample is measured by HPLC to calculate a conversion collection amount of aglycone (Table 6). Aglycone of about 25% can be collected by treatments of 200° C.×5 minutes and 240° C.×1 minute.

TABLE 6

| Treatment temperature | Treatment time | Oleuropein concentration (%) | Aglycone concentration (%) | Conversion collection rate[1] |
|---|---|---|---|---|
| Untreated | | 41 | 22 | 0 |
| 200° C. | 5 min. | 0 | 34 | 28 |
| 240° C. | 1 min. | 0 | 33 | 26 |
| | 5 min. | 0 | 23 | 3 |

[1]Conversion collection rate = 100 × [(Already treated aglycone concentration) − (Untreated aglycone concentration)]/[Untreated oleuropein concentration − Already treated oleuropein concentration]

INDUSTRIAL APPLICABILITY

Compared with glycoside bound to sugar residue, aglycones are high-value-added product because of their increased body absorption and physiological activity, and their decreased intake amount by a portion of sugar residues. Specifically, saponin has physiological actions such as cholesterol reduction, immunostimulation, antitumoral activity, and antimutagenic activity. Having a female hormone like action, soybean isoflavone aglycone is effective as therapeutic medicines for female diseases such as osteoporosis, menopause disorder, and breast cancer. Rutin aglycone is expected to have antiviral action. Aglycones such as digitoxin, lanatoside C, deslanoside, digoxin, methyldigoxin, and ouabain are useful as a cardiotonic drug. Strophanthin aglycone can be extremely useful cardiac stimulant. Glycyrrhizard aglycone is used for medication as well. Arbutin aglycone is used as diuretic and also contributes to whitening effect (cosmetic material) due to an action of interfering with tyrosinase involved in melanin synthesis. Sinigrin aglycone is expected to be used for medication.

DESCRIPTION OF THE REFERENCE NUMERALS

10 High temperature high pressure water reaction apparatus;
11 Water tank;
12 Water pump;
13 Heater;
14 Ingredient tank;
15 Slurry pump;
16 Heat/pressure resistant pipe for high temperature high pressure water reaction;
17 Cooler;
18 Filter;
19 Back pressure valve;
20 Batch-type reaction apparatus;
21 Pressure/heat resistant pipe;
22 Salt bath;
23 Basket;
24 Agitator; and
A Aglycone

What is claimed is:

1. A method for producing aglycone by bringing an O-glycoside into contact with high temperature high pressure water, characterized in that the high temperature high pressure water has a temperature from 150 to 320° C. and has a pressure not lower than a saturated water vapor pressure corresponding to the temperature provided that said temperature is from 240 to 320° C. in the case that the glycoside is soybean saponin.

2. The method for producing aglycone according to claim 1, wherein the glycoside is at least one type of a group comprising flavonoid glycoside, terpenoid glycoside, steroid glycoside, quinone glycoside, and lignan glycoside.

3. The method for producing aglycone according to claim 1, wherein the glycoside is soybean saponin and/or soybean isoflavone.

4. The method for producing aglycone according to claim 1, wherein the glycoside is oleuropein.

5. The method for producing aglycone according to claim 1, wherein time of contact between the glycoside and the high temperature high pressure water is from 0.5 to 20 minutes.

* * * * *